United States Patent
Reisman

(10) Patent No.: US 9,179,834 B2
(45) Date of Patent: Nov. 10, 2015

(54) ATTENUATION-BASED OPTIC NEUROPATHY DETECTION WITH THREE-DIMENSIONAL OPTICAL COHERENCE TOMOGRAPHY

(71) Applicant: Kabushiki Kaisha TOPCON, Tokyo (JP)

(72) Inventor: Charles A. Reisman, Mamaroneck, NY (US)

(73) Assignee: KABUSHIKI KAISHA TOPCON, Tokyo (JP)

( * ) Notice: Subject to any disclaimer, the term of this patent is extended or adjusted under 35 U.S.C. 154(b) by 0 days.

(21) Appl. No.: 14/168,303

(22) Filed: Jan. 30, 2014

(65) Prior Publication Data
US 2014/0218686 A1    Aug. 7, 2014

Related U.S. Application Data

(60) Provisional application No. 61/759,687, filed on Feb. 1, 2013.

(51) Int. Cl.
| | |
|---|---|
| *A61B 3/10* | (2006.01) |
| *A61B 3/14* | (2006.01) |
| *A61B 3/00* | (2006.01) |
| *G06T 7/00* | (2006.01) |

(52) U.S. Cl.
CPC .............. *A61B 3/0025* (2013.01); *A61B 3/0058* (2013.01); *A61B 3/102* (2013.01); *G06T 7/0012* (2013.01); *G06T 2207/10101* (2013.01); *G06T 2207/30041* (2013.01)

(58) Field of Classification Search
USPC ........... 351/200–246; 600/356, 400, 318, 558
See application file for complete search history.

(56) References Cited

U.S. PATENT DOCUMENTS

| | | | |
|---|---|---|---|
| 6,293,674 B1 | 9/2001 | Huang et al. | |
| 7,222,961 B2* | 5/2007 | Soliz et al. | .... 351/200 |
| 7,301,644 B2 | 11/2007 | Knighton et al. | |
| 7,505,142 B2 | 3/2009 | Knighton et al. | |
| 7,512,436 B2* | 3/2009 | Petty et al. | .... 600/476 |
| 7,659,990 B2 | 2/2010 | Knighton et al. | |
| 7,668,342 B2 | 2/2010 | Everett et al. | |
| 7,924,429 B2 | 4/2011 | Knighton et al. | |
| 8,073,202 B2 | 12/2011 | Everett et al. | |
| 8,208,688 B2 | 6/2012 | Everett et al. | |

(Continued)

OTHER PUBLICATIONS

Faber, Dirk J. et al. "Quantitative measurement of attenuation coefficients of weakly scattering media using optical coherence tomography" IN: Optics Express, Sep. 20, 2004, vol. 12, No. 19, pp. 4353-4365.

(Continued)

*Primary Examiner* — Mohammed Hasan
(74) *Attorney, Agent, or Firm* — Pearne & Gordon LLP

(57) ABSTRACT

Optical coherence tomography (OCT) scan data of a subject is acquired over a region of interest which can include an optic disc or a macula of a retina. Layer boundaries of retinal layers are identified in the OCT scan data to facilitate measurements. In one aspect, a measurement related to ratio value between a total backscattered signal intensity of one or more target layers of the retina and a total backscattered signal intensity of one or more reference layers is computed on a location-by-location basis within a region of interest of the OCT scan data. Measurements can be collected, aggregated, analyzed, and displayed in connection with other information taken or derived from the OCT scan data.

32 Claims, 6 Drawing Sheets

(56) References Cited

U.S. PATENT DOCUMENTS

| | | |
|---|---|---|
| 8,319,974 B2 | 11/2012 | Knighton et al. |
| 8,416,991 B2 | 4/2013 | Everett et al. |
| 8,913,793 B2 | 12/2014 | Everett et al. |
| 2012/0274896 A1 | 11/2012 | Vermeer et al. |

OTHER PUBLICATIONS

Van Der Meer, F.J., "Vascular applications of quantitative optical coherence tomography" IN: Downloaded from UvA-Dare, the institutional repository of the University of Amsterdam (UvA), Nov. 1, 2005.

Xu, Ch Enyang et al. "Characterization of atherosclerosis plaques by measuring both backscattering and attenuation coefficients in optical coherence tomography" IN: Journal of Biomedical Optics, May/Jun. 2008. vol. 13, No. 3, pp. 034003-1-034003-8.

Vermeer, K.A. et al. "Retinal Nerve Fiber Layer Attenuation Coefficient Maps Derived From Volumetric OCT Data" IN: Rotterdam Ophthalmic Institute, No. 798, May 6, 2012.

Van Der Schoot, Josine et al., "The Effect of Glaucoma on the Optical Attenuation Coefficient of the Retinal Nerve Fiber Layer in Spectral Domain Optical Coherence Tomography Images" IN: Investigative Ophthalmology and Visual Science, Apr. 2012, vol. 53, No. 4 pp. 2424-2430.

Vermeer, Koenraad A. et al. "RPE-Normalized RNFL Attenuation Coefficient Maps Derived from Volumetric OCT Imaging for Glaucoma Assessment" IN: Investigative Ophthalmology and Visual Science, Sep. 2012, vol. 53, No. 10 pp. 6102-6108.

Vermeer, K.A. et al. "Quantitative RNFL attenuation coefficient measurements by RPE-normalized OCT data" IN: Proceedings of SPIE, vol. 8209, Feb. 2012, pp. 82090U1-82090U-6.

European Search Report for EP 14 15 3444 dated Oct. 27, 2014.

\* cited by examiner

ATTENUATION-BASED OPTIC NEUROPATHY DETECTION WITH THREE-DIMENSIONAL OPTICAL COHERENCE TOMOGRAPHY

CROSS-REFERENCE TO RELATED APPLICATIONS

This application claims priority to U.S. Provisional Application Ser. No. 61/759,687, filed on Feb. 1, 2013, entitled "INTEGRATED ATTENUATION-BASED OPTIC NEUROPATHY DETECTION WITH THREE-DIMENSIONAL OPTICAL COHERENCE TOMOGRAPHY", the entirety of which is incorporated herein by reference.

BACKGROUND OF THE INVENTION

1. Field of the Invention

This application relates generally to optical diagnostic methods and apparatus and, more specifically, to an optic neuropathy detection method and apparatus utilizing optical coherence tomography.

2. Description of Related Art

Conventional diagnostics for eye disorders typically include a detailed ophthalmic examination of the retina. For initial examination, an eye doctor will view the retina through an ophthalmoscope. For a permanent record, the retina is typically photographed with a fundus camera. A fundus photograph directly records various anatomical features of the retina, such as the optic disc, fovea, blood vessels, and lesions. The imaging capabilities of fundus photography may be enhanced by supplementary techniques. A high-contrast image of retinal blood vessels, for example, can be photographed after the injection of a fluorescent dye into the bloodstream. The resulting image is referred to as a fluorescein angiogram.

More sophisticated techniques have been developed for diagnostics of the eye. One such technique is three-dimensional optical coherence tomography (3D OCT). In this technique, a light beam is directed onto the retina. Part of the beam is back-reflected, and interferometric analysis of the back-reflected light yields information on the structure of the retina. By varying optical parameters of the light probe, features at different depths below the surface of the retina may be analyzed. With this process, an image of a cross-section of the retina may be generated by scanning the optical probe along a line on the retina. By rastering the optical probe across the surface of the retina, a series of cross-sectional images may be produced. The series of cross-sectional images may be used to characterize the 3D structure of the retina, and parameters, such as local retinal thickness, etc., may be measured by 3D OCT.

Analysis of the thickness of the retina can be used to diagnose certain diseases of the eye, such as glaucoma. One indication of the health of the eye can be provided by comparing the retinal thickness of the patient's eye with reference data acquired from a population of healthy eyes. Progression of eye disease can also be monitored by measuring changes in retinal thickness over a period of time.

For example, a conventional approach is to utilize a circumpapillary scan to detect glaucoma and monitor a progression of glaucoma in a patient. A circle scan is performed around the optic disc at a fixed diameter. From the scan data, a thickness of the retinal nerve fiber layer (NFL) around the circle is measured.

Attempts have been made to derive other measurements which can be applicable to detecting optic neuropathy, such as glaucoma. Specifically, focus has been on measurements that can indicate glaucoma prior to measurable changes in retinal layer thicknesses. In one proposal, optical properties of the retinal NFL are calculated. In particular, an attenuation coefficient, which characterizes how rapidly intensity of light is attenuated as the light propagates through a medium (e.g., a scattering or absorbing medium), is one such optical property. It is suspected that changes in the attenuation coefficients of the retinal nerve fiber layer tissue can be detected prior to observable thinning typical with glaucoma.

However, attenuation coefficients are highly dependent on location, including in the axial direction, such that the attenuation coefficient can vary even within a particular tissue layer. Accordingly, an average coefficient value, e.g. calculated over a depth or thickness of the tissue layer but corresponding to a fixed and predefined depth such as the axial dimension length associated with a single pixel, is often utilized as a representative value for the tissue layer for a given X-Y location (A-line). Thus, this locationality of attenuation coefficients results in an indirect or proxy relationship to underlying physical reality associated with optic neuropathies. For instance, the attenuation calculation described produces results which are decorrelated from thickness. While attenuation coefficient measurements could correlate with a diagnosis of glaucoma, a thickness-based technique may be equally, and possibly more, effective.

BRIEF SUMMARY OF THE INVENTION

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of the summary is to present some concepts related to some exemplary non-limiting embodiments in a simplified form as a prelude to the more detailed description of the various embodiments that follow.

In various, non-limiting embodiments, 3D OCT scan data of a subject is acquired over a region of interest which can include an optic disc or a macula of a retina. Layer boundaries of retinal layers are identified in the 3D OCT scan data to facilitate measurements of characteristics. In one aspect, a measurement related to ratio value between a total backscattered signal intensity of one or more target layers of the retina and a total backscattered signal intensity of one or more reference layers is computed on a location-by-location basis within a region of interest of the 3D OCT scan data. Measurements can be collected, aggregated, analyzed, and displayed in connection with other information taken or derived from the 3D OCT scan data.

These and other embodiments are described in more detail below.

BRIEF DESCRIPTION OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
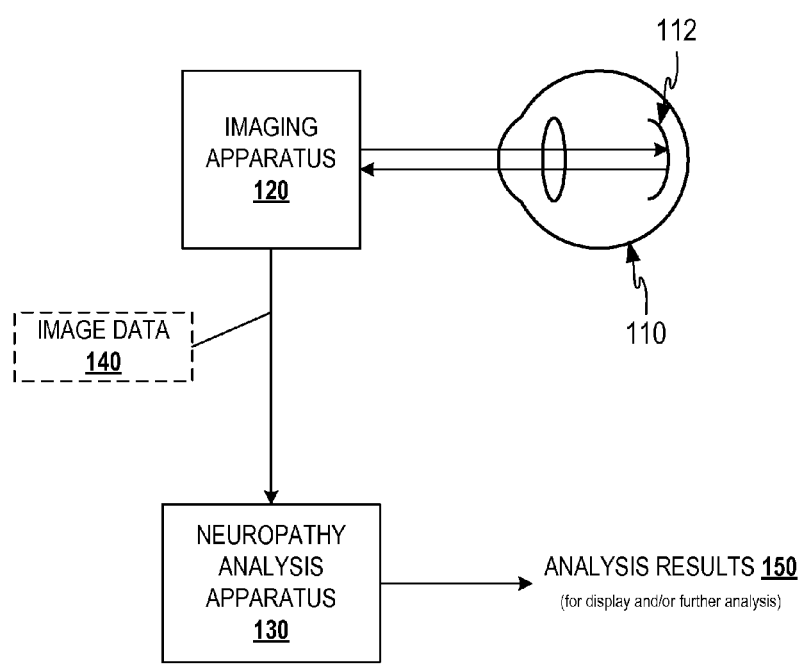
FIG. 1 illustrates an exemplary, non-limiting system for detecting and measuring optic neuropathies of an eye.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

Diseases such as glaucoma, multiple sclerosis (MS), etc., can present as an optic neuropathy in which nerve tissue in a retina of an eye is destroyed. While other techniques are available to diagnose and monitor optic neuropathies (e.g., pressure estimates within the eye, visual field tests, optic head analyzers that measure cup-to-disc ratio, etc.), optical coherence tomography (OCT) is shown to enable earlier detection and fine measurements of disease progression. For example, taking glaucoma as an exemplary disease that presents as an optic neuropathy, increased pressure and/or tension within the eye can cause nerve fiber axons to kink and die and/or ganglion cells to die. Thus, over time, glaucoma causes atrophy in the nerve fiber layer (NFL), the ganglion cell layer (GCL), and the inner plexiform layer (IPL). Typically, NFL damage assumes the form of an arcuate shape centered on an optic disc of the eye and extending to a more temporal location, relative to the optic disc. GCL damage is often seen in the macula of the eye, often within the ring of tissue surrounding the fovea where the GCL is at or near its thickest. The NFL and GCL damage typically presents as a thinning of the layers in the respective areas. Conventionally, a circumpapillary scan technique is utilized to detect glaucoma and monitor a progression of glaucoma in a patient. In this conventional approach, a circle scan is performed around the optic disc at a diameter of approximately 3.4 mm (specifically, in the range of 3.0 to 3.45 mm). From the scan data, a thickness of the circumpapillary NFL around the circle is measured. However, an OCT scan is capable of quantifying the NFL and GCL damage, or changes in other layers, groups of layers, etc., in terms of other measurable parameters in addition to layer thicknesses.

According to one or more aspects described herein, a measurement derived from optical properties can be utilized in connection with an OCT scan. Similar to changes in tissues thickness and/or tissue mass, optic neuropathies alter the optical properties of retinal tissues. Specific optical properties, such as attenuation coefficients, integrated attenuation values, etc., can be measured and/or estimated for specific tissues (i.e., retinal layers) based on OCT scan data. However, these optical properties are related, generally monotonically, to relative backscattering between disparate groups of tissues. Accordingly, while the optical properties described above have underlying physical or physiological meanings, substantially any measured quantity which relates to the relative backscattering can be utilized for diagnosis of optic neuropathies.

In one embodiment, a method for detecting and monitoring an optic neuropathy of a retina is described herein. The method includes obtaining imaging data of a region of the retina; identifying boundaries between layers of the retina in the region based on the imaging data; and determining, on a location-by-location basis for at least a portion of the region of the retina, a measurement value related to a ratio value between a total backscattered signal intensity of one or more target layers of the retina and a total backscattered signal intensity of one or more reference layers to generate a set of measurement values for locations in the portion of the region of the retina.

In an example, the measurement value is monotonic with respect to the ratio value. For instance, the measurement value is an integrated attenuation value determined according to the following relation:

$$\mu_{ATT} d = \frac{\log(R/\beta + 1)}{2}, \quad (1)$$

where $\beta$ is modeled as a substantially constant value, R is the ratio value, and $\mu_{ATT} d$ is the measurement value and represents a total attenuation of light over a depth d of the retina. In some cases, d may be effectively kept constant by, for example, integrating over a fixed depth or taking the mean of the integration, which is mathematically equivalent to integrating over fixed depth except that another constant (such as $\beta$) would be made to reflect the induced scaling factor. Further to this example, the method can include standardizing a depth over which the total backscattered signal intensity of the one or more reference layers is determined from location to location. The standardizing facilitates maintaining $\beta$ as a constant value. Moreover, the ratio value R for a particular location, with standardization of the depth over which the total backscattered signal intensity of the one or more reference layers, is given by:

$$R = \frac{T_{IRL}}{T_{ref}} \quad (2)$$

$$\approx \frac{\sum_{z=1}^{d_{IRL}} T_{IRL}(z)}{\frac{1}{d_{ref}} \sum_{z=1}^{d_{ref}} T_{ref}(z)},$$

where $T_{IRL}(z)$ is a signal intensity of a backscattered signal from the one or more target layers at depth z, $T_{ref}(z)$ is a signal intensity of a backscattered signal from the one or more reference layers at depth z, $d_{IRL}$ is a thickness of the one or more target layers, and $d_{ref}$ is a thickness of the one or more reference layers. It should be noted that in equation 2, z in the numeration refers to a pixel of the inner retinal layer (IRL); whereas, z in the denominator refers to a pixel of the reference layer.

According to other examples, the one or more target layers include a retinal nerve fiber layer, a ganglion cell layer, an inner plexiform layer, or combinations thereof; the one or more reference layers include a retinal pigment epithelium; and the region of the retina may include an optic disc and/or a macula of the retina. In addition, the imaging data can comprise three-dimensional optical coherence tomography scan data. The method can additionally include displaying information derived from at least one of the set of measurement values or the imaging data, wherein displaying the information comprises displaying a visual representation of the set of measurement results as an overlay on image generated from the imaging data. Furthermore, the method can include respectively comparing measurement values from the set of measurement values to one or more thresholds; and calculating a probability of an optic neuropathy based on comparison results. The one or more thresholds are pre-determined from a normative database.

According to another embodiment, a method is described herein that includes acquiring three-dimensional optical coherence tomography (3D OCT) scan data for a region of interest of the retina; segmenting the 3D OCT scan data to identify layer boundaries between layers of the retina; calculating, based on segmented 3D OCT scan data, a set of measurement values over at least a portion of the region of interest on a location-by-location basis, measurement values, of the set of measurement values, being based on ratio values, for respective locations, between a total backscattered signal intensity of one or more target layers of the retina and a total backscattered signal intensity of one or more reference layers. In one example, the set of measurement values are a set of attenuation coefficients calculated location-by-location. In another example, the set of measurement values are a set of integrated attenuation values calculated location-by-location. The method can further include comparing the set of measurement values to normative data; and outputting a probability of an optic neuropathy based on a result of comparing the set of measurement values to normative data. Constructing the normative data can include collecting a plurality of OCT scans on a plurality of confirmed normal subjects, aggregating measurements from the plurality of OCT scans, and statistically compiling aggregated measurements. In addition, the method can include identifying a disease associated with the optic neuropathy.

In yet another embodiment, an OCT imaging system is described herein. The OCT imaging system can include an imaging apparatus for capturing OCT scan data of a region of interest of a retina. In addition, the OCT imaging system can include a neuropathy analysis apparatus comprising a processor and a non-transitory, computer-readable medium having stored thereon on computer-executable instructions, the computer-executable instructions causing the processor to compute, location-by-location over the OCT scan data, a set of measurement values based on ratio values, for respective locations, between a total backscattered signal intensity of one or more target layers of the retina and a total backscattered signal intensity of one or more reference layers. The region of interest includes an optic disc and a macula of the retina. The set of measurement values is a set of integrated attenuation values relative to the one or more target layers of the retina.

FIG. 1 illustrates an exemplary, non-limiting system 100 for detecting and/or measuring optic neuropathy in an eye 110. Particularly, system 100 includes an imaging apparatus 120 configured to generate image data 140 corresponding to a region of interest 112 of the eye 110, such as the retina or a portion thereof for example. According to one example, the region of interest 112 can be an optic disc of the eye 110 in order to detect optic neuropathy associated with glaucoma. In another example, imaging apparatus 120 scans a macula of the eye 110 as the region of interest to facilitate detection and/or monitoring of multiple sclerosis, macular degeneration, etc. A scan of the macula may also be indicative of an optic neuropathy, since the NFL fibers that connect to and from the optic disc are axons of the ganglion cells. It is also to be appreciated that a scan of the macula can facilitate detection and monitoring of glaucoma. In another example, imaging apparatus 120 scans both the optic disc and macula within the same scan.

In accordance with an example, imaging apparatus 120 can be an OCT apparatus and will generally be discussed as such to facilitate explanation of aspects provided herein. However, it is to be appreciated that the subject matter is not limited to application only with OCT and that the aspects described herein can be utilized in connection with other imaging modalities such as, but not limited to, computed tomography (CT), magnetic resonance imaging (MRI), ultrasound, etc.

OCT is an imaging technique capable of acquiring sub-surface images of a subject at micrometer resolutions. For instance, in ophthalmological applications, OCT is utilized to generate cross-sectional images of portions of an eye, including the retina. In general, OCT operates according to the same basic principles as ultrasound but utilizes light as a medium whereas ultrasound utilizes sound. That is, OCT images the subject by irradiating the subject with light and measuring a time delay and intensity of reflected light. However, light is much faster than sound. So, unlike the time delay in an ultrasound echo, the time delay of the reflected light is not directly measured. Instead, OCT utilizes low-coherence interferometry to detect time differences corresponding to distances between structures of the subject. Particularly, a low-coherence broadband light source is split into a sample portion and a reference portion. The reference portion travels a path toward a reference (i.e., a reference mirror) while the sample portion is directed towards the subject (e.g., an eye and, specifically, the retina). When a distance traveled by the sample portion and a corresponding reflection off the subject is within a coherence length of a distance travelled by the reference portion and its corresponding reflection, an interference pattern is generated. The interference pattern indicates an intensity of light at a certain depth of the subject, which in turn, facilitates generating image data pertaining to the subject.

To derive intensity information at varying depths of the subject, several different techniques can be utilized. In one technique, referred to as time-domain OCT, the travel distance of the reference portion is modulated to scan different depths. For example, the reference mirror can be oscillated to change the travel distance. Other techniques, which can be collectively referred to as frequency-domain OCT, do not require alterations to the reference portion. In these techniques, various frequencies of light can be encoded, spatially or temporally for example, where different detected frequencies of reflected light correspond to different depths within the subject. A Fourier analysis on a received signal that represents reflected intensities at different frequencies generates the intensities reflected at different depths at a point of the subject.

According to one example of a frequency-domain OCT technique (commonly referred to as Fourier-domain or spectral-domain OCT), a reference interference pattern is dispersed into individual frequency components by a grating or other such dispersive means. Conceptually, an array of photodetectors, each sensitive to a specific range of frequencies, simultaneously detects respective intensities of the frequency components corresponding to different depths at a scanned point of the subject. In conventional practice, however, typically a charge couple device (CCD) or complimentary metal-oxide-semiconductor (CMOS) line camera or spectrometer is utilized and the grating physically separates the different wavelengths of light. In another example, referred to as swept-source OCT, a tunable light source is utilized to scan over different frequencies. The intensities at each scanned frequency can be collected and transformed by a Fourier analysis to generate an intensity profile that details intensities at various depths.

A plurality of points or locations of the region of interest 112 can be scanned by the imaging apparatus 120 to generate a plurality of corresponding A-scans. Each A-scan provides a respective intensity profile within the region of interest 112 at the corresponding location. A series of A-scans can be assembled to collectively form a cross-sectional image of the region of interest 112, which is also known as a B-scan. For instance, A-scans associated with points along some arbitrary path on the region of interest 112 can be aggregated to generate a cross-sectional image, along the arbitrary path, of the region of interest 112. According to one embodiment, the imaging apparatus 120 is directed to physically scan the region of interest 112 along the arbitrary path to acquire the A-scans. In another embodiment, however, the imaging apparatus 120 acquires A-scans for an area of the region of interest 112 (such as an entirety thereof) that contains the arbitrary path. Subsequently, a B-scan along the arbitrary path can be extracted from the A-scan information. The B-scan, generated using this technique, can be referred to as a virtual or simulated scan since the imaging apparatus 120 is not directly scanning the arbitrary path.

A plurality of B-scans, along parallel cross-sections for instance, can be assembled to provide a three-dimensional (3D) scan image of the volume of the region of interest 112. Various slices of the 3D scan image can be computed and are typically referred to as C-scans. For example, C-scans corresponding to en face images of retinal layers or of the fundus of the eye 110 can be computed from the 3D scan image (or 3D scan data underlying the 3D scan image).

As utilized herein, 3D scan data can refer to a set of A-scans for a region of interest, one or more B-scans derived from A-scans of the set, one or more C-scans derived from the A-scans and B-scans, or the like. In an aspect, image data 140, provided to a neuropathy analysis apparatus 130 by the imaging apparatus 120, can be 3D scan data. It is to be appreciated that image data 140 can also include supplementary information in addition to the 3D scan data. For example, the imaging apparatus 120 can be capable of acquiring a fundus image in addition to OCT image data. In such cases, the fundus image can be acquired by scanning laser ophthalmoscopy, a fundus camera, or the like. However, it is to be appreciated that the fundus image can be generated from the 3D scan data by, for instance, summing every pixel in every A-scan.

From image data 140, and particularly the 3D scan data included therein, various measurements and quantifications can be determined. Accordingly, neuropathy analysis apparatus 130 is configured to evaluate image data 140, calculate measurements, and output analysis results 150 for display or further analysis. In one example, measurements can include layer thicknesses of individual layers (e.g., NFL, GCL, inner plexiform layer (IPL), etc.), of combinations of layers (e.g., GCL and IPL (GCL+); NFL, GCL, and IPL (GCC), etc.), or of all retinal layers. In another example, measurements can include attenuation coefficients (i.e., a measure of a degree to which light attenuates while passing through a layer) or other image-derived coefficient measures (e.g., polarization, possibly measured by polarization sensitive OCT; magnitude; phase, etc.).

However, according to an exemplary, non-limiting embodiment of the neuropathy analysis apparatus 130, the measurement derived from image data 140 can be an integrated attenuation measurement. The integrated attenuation measurement, according to one aspect, relates to the attenuation coefficient described above. Specifically, an estimate of the attenuation coefficient ($\mu_{ATT}$) can be conventionally given by the following equation:

$$\mu_{ATT} = \frac{\log(R/\beta + 1)}{2d}, \tag{3}$$

where $\beta$ is assumed to be a constant value, R represents a ratio value described in greater detail below, and d is a depth measure indicating the depth over which an average attenuation coefficient is taken to produce the estimate. An integrated attenuation value ($\mu_{ATT}d$) can be calculated according to the following relation:

$$\mu_{ATT}d = \frac{\log(R/\beta + 1)}{2} \tag{4}$$

Conceptually, the former relationship has units of distance$^{-1}$ (e.g., mm$^{-1}$) and represents an average attenuation coefficient over a depth, d, such as a retinal layer. The latter relationship is unit-less and represents an integrated attenuation over a depth (i.e., over a layer, a group of layers, etc.). That is, equation 3 provides a measure (attenuation coefficient) representing an average rate of attenuation (i.e., attenuation per unit distance) over some distance, d. The distance, over which the rate of attenuation is averaged to provide the attenuation coefficient, is typically associated with a thickness of a retinal NFL layer, for example, as glaucoma typically presents as an atrophy of this layer of the eye. In contrast, the integrated attenuation measure is not a locational property but rather an aggregate property or a characteristic over depth. Further, an integrated attenuation measurement can be utilized as a proportional estimate of total layer tissue mass due to the employment of optical properties in combination with physical properties (i.e., thickness) and, thus, potentially be more diagnostically relevant. The attenuation coefficient is a proxy of tissue density and, likely, not more effective than conventional thickness-based analyses in detection and monitoring of optic neuropathies.

According to another aspect, neuropathy analysis apparatus 130 can calculate the integrated attenuation value ($\mu_{ATT}d$), A-line by A-line, over an entirety of image data 140. However, it is to be appreciated that neuropathy analysis apparatus 130 can calculate integrated attenuation values for a subset of image data 140 corresponding to specific areas the region of interest 112 selected by a user, for example. The specifics of the calculation are detailed below.

Neuropathy analysis apparatus 130 can utilize normative databases to facilitate identification of optic neuropathies from the measurements taken over image data 140. Normative databases facilitate identifying outlier cases while also identifying probable regions of atrophy. In one aspect, neuropathy analysis apparatus 130 can construct normative databases by executing OCT scans on a large number of confirmed normal subjects, aggregating measurements from the scans, and statistically compiling the results. In another aspect, normative databases already generated can be provided to neuropathy analysis apparatus 130 to utilize in connection with patient scan data and corresponding measurements. For example, the neuropathy analysis apparatus 130 utilizes the normative databases to identify locations where the corresponding measurement triggers thresholds (e.g., $p<0.05$, $p<0.01$, etc.). Accordingly, a display, such as an OCT-derived map, can be generated having green areas (likely normal), yellow areas (questionable, e.g. $p<0.05$), and red areas (likely disease conditions, e.g. $p<0.01$). Here, p is a probability that a statistical null hypothesis is not disproven and can be calculated from a comparison against the normative data or via a statistical test (e.g., a binomial distribution). Accordingly, for example, $p<0.01$ indicates less than a one percent chance that the samples are statistically indistinguishable. It should be appreciated that the specific values of p used in the above example to determine if a pixel is green, yellow or red are merely examples, and other values can be used as deemed appropriate.

Thus, comparison results to the normative databases, a generated 3D volume corresponding to a volume of the region of interest, measurement values, summary statistics (e.g., mean, median, standard deviation, etc.) of measurement values, image data 140 or portion thereof, can all be combined in total or in part to generate analysis results 150 for display and/or further analysis.

For example, analysis results 150 can include display data representing various B-scans, C-scans, OCT-derived maps, etc. The various scans can be accompanied by measurement results and/or typical red/yellow/green normative analysis results. In another example, measurement results can be represented as overlays with an OCT-derived map, such as a thickness map, projection image, integrated attenuation map, etc., or an image acquired from an alternative modality (e.g., scanning laser ophthalmoscopy, fundus camera, etc.).

Figure 2:
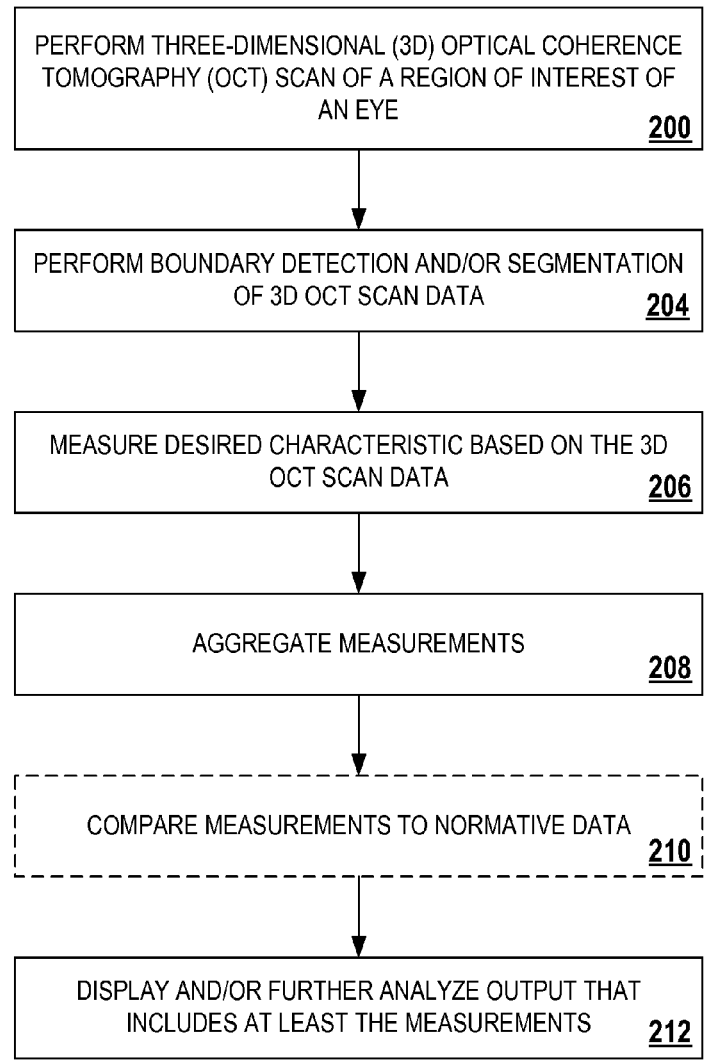
FIG. 2 is a flow diagram of an exemplary, non-limiting embodiment for diagnosing and/or monitoring optic neuropathies of an eye using optical coherence tomography.

Turning to FIG. 2, illustrated in an exemplary, non-limiting process of utilizing 3D OCT scans to facilitate diagnosis, monitoring and/or treatment of optic neuropathies. This process can be carried out, for example, by system 100 described above with reference to FIG. 1. At 200, a 3D OCT scan of a region of interest of an eye of a patient is performed. As a result of the scan, 3D OCT scan data is generated. The 3D OCT scan data can include a plurality of A-scans corresponding to coordinates (e.g., x-y coordinates) of the region of interest, B-scans computed from a set of A-scans, C-scans computed from A or B-scans, or complete 3D volume data of the region of interest. The region of interest can cover substantially any portion of the eye or retina of the eye including, specifically, the optic disc, the macula, or both the optic disc and macula simultaneously. The OCT apparatus performing the scan can be any one of a time-domain OCT, spectral-domain OCT, or swept-source OCT. In addition, the 3D OCT scan data can undergo pre-processing such as downsampling or a three-dimensional affine transformation to re-orient the scan data.

At 204, layer boundaries, which are relevant for desired measurements, are detected within the 3D OCT scan data. The layer boundaries enable measurements, such as thickness measurements, to be calculated. Further, layer boundaries delimit regions over which attenuation calculations are integrated. By way of example, segmentation can identify the boundaries of the retinal NFL, GCL, IPL, retinal pigment epithelium (RPE), outer plexiform layer, inner segments/outer segments (IS/OS) junction, choroid, sclera, or any other retinal layers, membranes, or boundaries.

At 206, measurements are calculated over layers of interest. In particular, measurements are calculated based on the 3D OCT scan data in accordance with layer boundaries detected at 204. The measurements, as described above, can include thickness measurements, attenuation coefficient or other image-derived coefficient measures, etc. According to one non-limiting, exemplary embodiment, the measurement calculated over the layers of interest is an integrated attenuation measurement based on equation 4 above. However, it is to be appreciated that the calculated measurement can be a generalized or abstracted measurement derived from the integrated attenuation relationship of equation 4, as described in greater detail below. In an aspect, the layers of interest can include the NFL, GCL, GCL+, GCC, or other combinations.

At 208, measurement data is aggregated and/or integrated over an aggregation region. Aggregation, according to an aspect, can involve summation, averaging, taking a quantile (e.g., maximum, median, minimum, etc.), or the like, of a collection of measurement values within the aggregation region. For example, the aggregation region can correspond to an entire scan area (i.e., the region of interest subject to the OCT scan); superior and/or inferior hemispheres; temporal, superior, nasal, and/or inferior quadrants; 45-degree shifted quadrants (i.e., temporal-superior quadrant, etc.); clock hours; or any other definable sub-region of the region of interest. At 210, the measurement data can optionally be compared to normative data as described above.

At 212, output data can be displayed. According to an aspect, the display can include the measurement results and the red/yellow/green, for example, normative analysis results on an A-line by A-line basis. The display can further include representations of the aggregate results (full area and/or sub-regions), including both summary statistics (e.g., mean and standard deviation) and normative analysis results. The output data can also be provided as a component within an analysis report geared towards glaucoma (and/or MS) detection, monitoring, or treatment. Further, the results can be displayed individually or can be co-registered and overlaid with an OCT-derived map (e.g., projection image, thickness map, etc.) or with another imaging modality.

Generalized Measurement for Optic Neuropathy Detection

As discussed previously, conventional approaches to diagnose glaucoma include measuring and/or estimating a thickness of a nerve fiber layer, as a proxy for layer mass, at various retinal locations. For example, such measurements or estimations can be derived from scanning laser polarimetry, or traditional OCT-based thickness quantification. However, as stated above, thickness is a proxy of layer mass, which can introduce inconsistency in neuropathy detection methodologies. For example, Müller glial cells serve, in part, as retinal support structure such that even as a mass of a retinal layer approaches zero (due to disease-related atrophy, for instance) in a particular location, an actual measurable thickness of a retinal layer may approach a non-zero asymptote level as opposed to going to zero. In another example, hypodense regions (i.e., holes) within a nerve fiber layer, as imaged by OCT, have been noted to be associated with atrophy induced by optic neuropathies. This further highlights that nerve fiber layer thickness and tissue mass do not fully correspond. Previous work involving attenuation coefficients suggests that changes in tissue properties might occur before measurable changes in layer thickness. However, attenuation coefficients, as mentioned above, suffer from a similar proxy relationship as layer thickness, albeit as a proxy to tissue density as opposed to tissue mass. Accordingly, a measurement that more closely corresponds to (i.e., better measures or estimates) total layer mass at a given retinal x/y location, would be expected to perform better in terms of optic neuropathy detection.

While the measurement provided above in equation 4 is such a measurement, the integrated attenuation measurement above can be further generalized so as to be functional to a greater range of optic neuropathy detection applications. First, it is assumed that β is constant. Accordingly, the only variable quantity in equation 4 is the ratio value, R. Moreover, the logarithmic transform of equation 4 has monotonic properties. Therefore, from a diagnostic viewpoint, equation 4 reduces to:

$$\mu_{ATT}d \approx f(R) \tag{5},$$

where the function, $f(x)$, is monotonic with x. Thus, $\mu_{ATT}d$ also has a monotonic relationship to R. It is to be appreciated that many disease detection schemes, including receiver operating characteristic (ROC) analyses, compare values to thresholds. In such schemes, rank-order is primarily significant. Accordingly, since a monotonic relationship exists above, an optic neuropathy detection scheme, based on integrated attenuation, can be implemented using the ratio value, R, (or any other factor that is a monotonic of R) by itself. That is, due to the monotonic relationship described above, the ratio value can be used as a proxy measurement for the integrated attenuation value, so long as β is substantially constant. In other words, a detection scheme can be implemented that is mathematically described according to the following:

$$g(\mu_{ATT}d) \approx R \tag{6}$$

As described above, R is a ratio value. In traditional attenuation coefficient applications (e.g., according to equation 3), R represents a ratio between a total backscattered signals from the nerve fiber layer and the retinal pigment epithelium, respectively. In other words, in traditional application, the ratio is given by the following:

$$R = \frac{T_{NFL}}{T_{RPE}}, \tag{7}$$

where $T_i$ represents a total backscattered signal from layer i. However, as utilized herein for integrated attenuation measurements, the ratio value is not so limited. For instance, the target layer is not limited to the retinal nerve fiber layer (NFL) as with previous applications. Other layers such as the ganglion cell layer (GCL), the inner plexiform layer (IPL), or combinations thereof, can be used in addition to the NFL (or in combination with the NFL). Generally speaking, a target layer can include any retinal layer that is inner to the reference layer (i.e., closer to a center of an eyeball relative to the reference layer) or combinations of other retinal layers inner to the reference layer. Further, the integrated attenuation measurement disclosed herein is not limited to utilizing the retinal pigment epithelium (RPE) as a reference layer. Other layers, for example, the inner plexiform layer, the outer plexiform layer, or the inner segments/outer segments (IS/OS) junction, can be utilized as the reference layer. It is also to be appreciated that combinations of layers can be utilized as a reference. As such, for integrated attenuation measurements according to equation 4 or for glaucoma detection functions according to equation 6, the ratio value R is given by:

$$R = \frac{T_{IRL}}{T_{ref}}, \tag{8}$$

where IRL refers to an inner retinal layer(s) and ref relates to the reference layer(s).

Results

Figure 3:
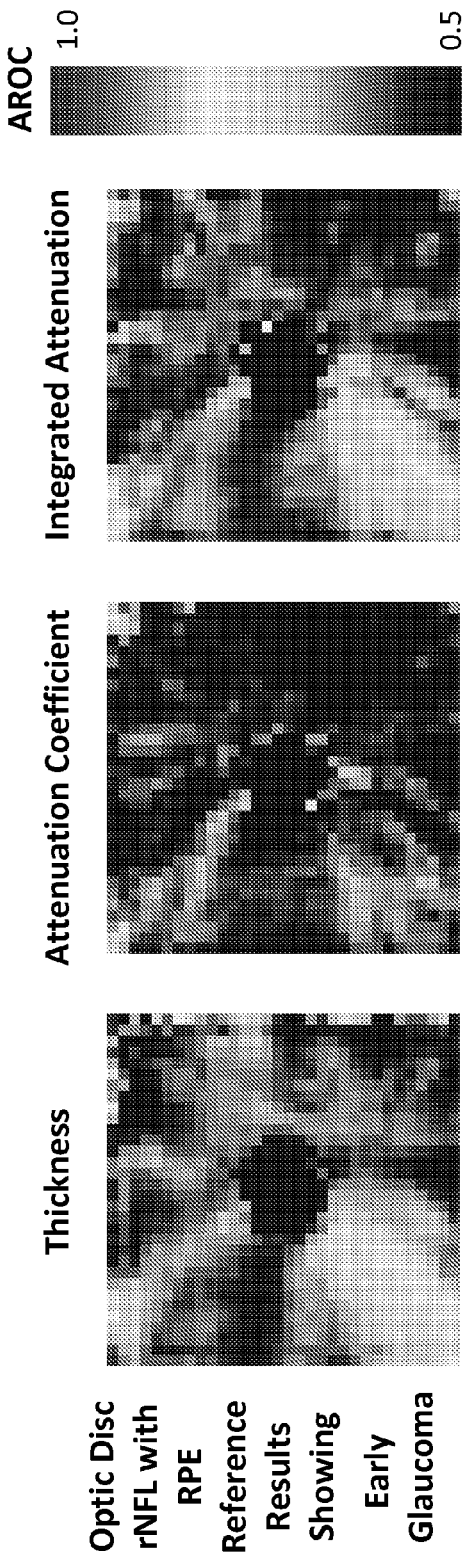
FIGS. 3 and 4 illustrate results of measurements on OCT scan data in terms of effectiveness in diagnosing glaucoma for various stages of the disease and locations within the retina.
Figure 4:
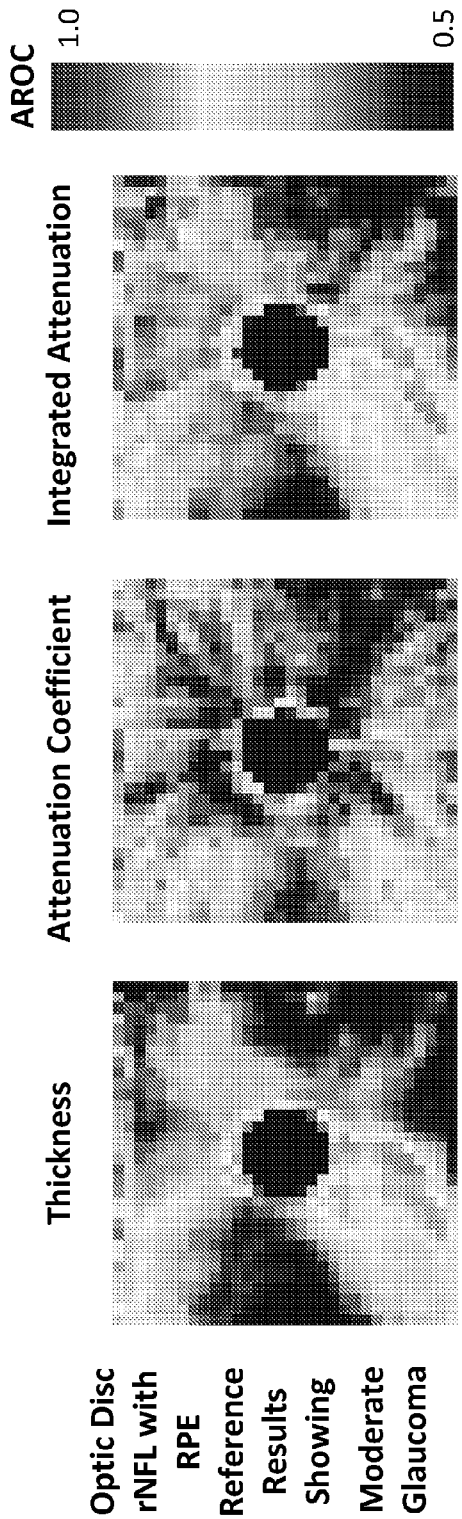

FIGS. 3 and 4 illustrate various results of optic neuropathy detection based on the concepts described herein. These results are presented in the form of receiver operating characteristic (ROC) maps. ROC maps, in general, present data (i.e., measurements) from OCT scan data for a group of patients in comparison to historical data of many control subjects in which each pixel in the resulting map represents the individual area under the curve result from an ROC analysis corresponding to that location. In particular, ROC maps reveal patterns in which a symptom historically manifests to indicate regions of interest that are reliable predictors of a condition, such as glaucoma. In the ROC maps for FIGS. 3 and 4, redder areas indicate locations for which the associated measurement is a good predictor of a condition, while blue regions are associated with poor predictive capabilities.

FIG. 3 depicts results for early stage glaucoma related to integrated attenuation measurements of the optic disc retinal NFL for the optic disc. FIG. 4 depicts results for moderate stage glaucoma related to integrated attenuation measurements of the retinal NFL for the optic disc.

With reference to FIGS. 3 and 4, the integrated attenuation methodology generally yields results that offer the best aspects of the individual thickness and attenuation coefficient results on a location by location basis. As can be seen from the example ROC maps, in some locations integrated attenuation tends to share more in common with thickness-based analysis, and in other locations with attenuation coefficient analysis. With reference to the ROC maps of the optic disc shown in FIGS. 3 and 4, the integrated attenuation results show a broader region of high AROC (area under the ROC curve) levels covering the inferior arcuate, especially in the moderate glaucoma case (FIG. 4). It should also be noted that in early glaucoma (FIG. 3) the integrated attenuation methodology has significantly higher AROC score levels than the attenuation coefficient based methodology. While the ROC maps of FIGS. 3 and 4 show the optic disc, ROC maps of other areas, such as the macula, can also be constructed.

Exemplary Optical Coherence Tomography System

Figure 5:
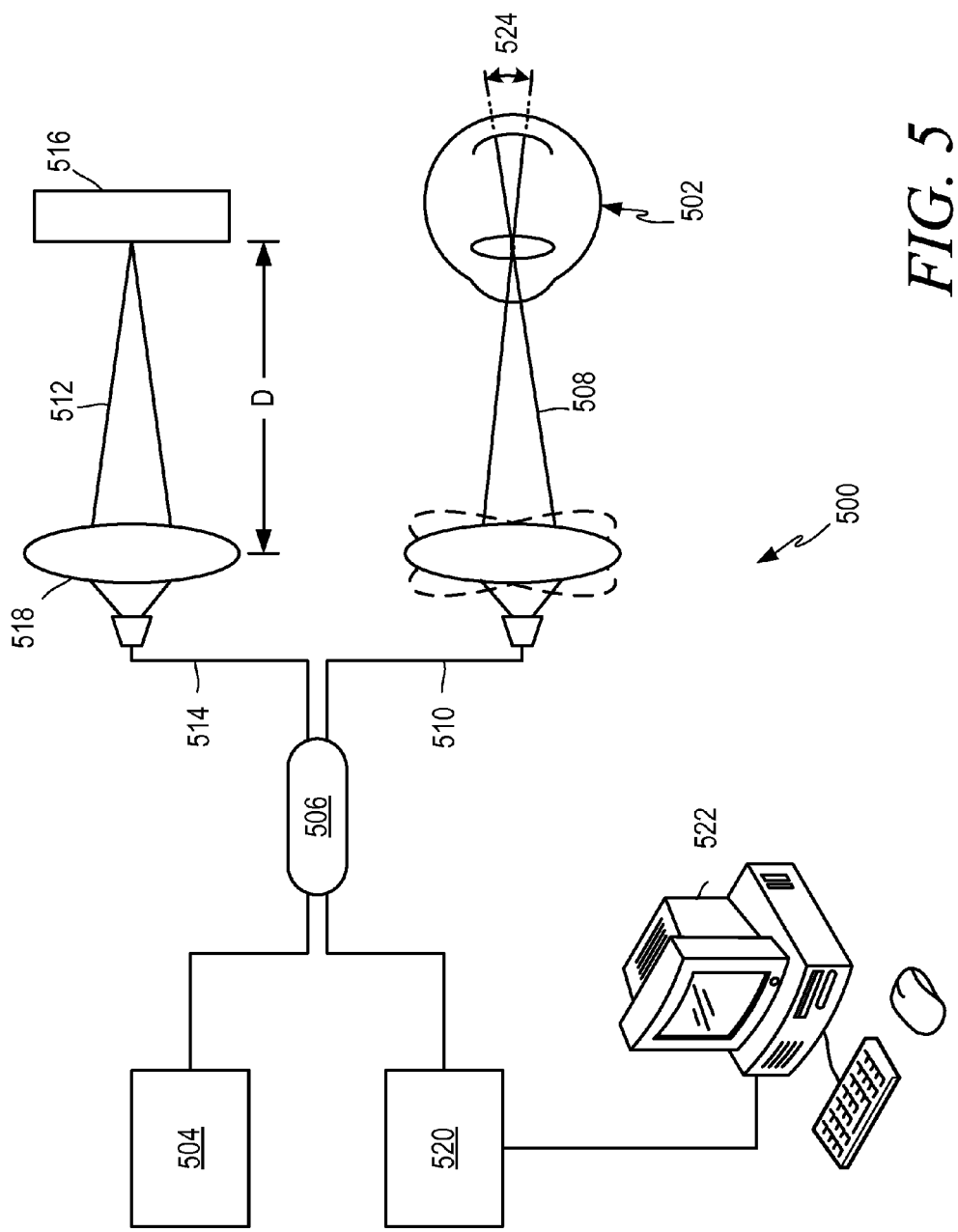
FIG. 5 illustrates a schematic diagram of an exemplary, non-limiting optical coherence tomography system in which one or more aspects of various embodiments herein can be implemented.

Turning to FIG. 5, illustrated is an exemplary, non-limiting embodiment of an optical coherence tomography (OCT) system 500 in which one or more aspects described above can be implemented. As shown, system 500 can perform an imaging technique used in ophthalmology to generate cross-sectional images of portions of an eye 502, such as the retina for example.

Generally, OCT involves impinging light from a low-coherence broadband light source 504 onto portions of the eye 502, and observing reflected light to generate a cross-sectional image of those portions of the eye 502. Light from the light source 504 is split by a an optical adaptor 506 such as a beam splitter, fiber coupler or the like, into two portions: a sample portion 508 that travels along a path 510 toward the eye 502, and a reference portion 512 that travels along a path 514 toward a reference reflector such as a mirror 516. The sample portion 508 and the reference portion 512 are at least partially reflected, and the reflected portions combined by the optical adaptor 506 and the intensity or other quality of the combined, reflected light is sensed by a detector 520 operatively connected to transmit a signal indicative of the sensed quality to be received by a computer 522. When the distance travelled by the sample portion 508 is within a coherence length of the distance travelled by the reference portion 512, an optical interference pattern is created, affecting the intensity of the reflected and combined light. The intensity of the combined, reflected light varies depending upon the properties (e.g., tissue backscattering, polarization, etc. . . . ) of the portions of the eye 502 that are illuminated by the sample portion 508. Information about such properties of the illuminated portion of the eye 502 can then be determined based on the intensity of the combined, reflected light, and used to generate image data pertaining to that illuminated portion of the eye 502.

The depth to which the sample portion 508 penetrates the eye 502 can be controlled in the time domain by varying a distance D separating a transmitter 518 of the reference portion 512 from the mirror 516. Alternatively, the depth of penetration can be controlled in the frequency domain by utilizing a broadband light source or alternatively sweeping the wavelength of the light source 504 over a range of frequencies. Though the distance D may be varied when depth is controlled in the frequency domain, such variance counterbalances saccadic eye movements or eye shape and is not intended to control scanning depth. Conducting a Fourier analysis on the combined, reflected light relates the light reflected at different frequencies to light reflected at different depths of the eye 508. Further, the mirror 516 can also be utilized to adjust penetration in a frequency-domain OCT scanner, albeit typically at a much lower rate than performed in a time-domain OCT scanner.

The sample portion 508 having a fixed penetration depth can be reflected through adjustment of a mirror, lens, etc. . . . , to various different orientations (illustrated using broken lines in FIG. 5) to illuminate different spatial locations over a region of interest 524 (e.g., macula, optic disc, etc. . . . ) within the eye 502. The intensity of the combined, reflected light (or other quality) sensed by the detector 520 is transmitted to the computer 522 shown in FIG. 5 for each different spatial location of the region of interest 524. The computer 522, which includes a processor for executing computer-executable instructions stored by a non-transitory, computer-readable medium such as a hard drive, for example, stores the sensed intensities in a database also stored on the hard drive. The database can be structured to store each value of the intensity sensed by the detector 520 with a link or other relationship to the respective different spatial location in the region of interest 524 from which the corresponding light was reflected. Similarly, the intensity values of light reflected from the different spatial locations, but for a different axial penetration depth of the sample portion 508 of the light into the region of interest 524, can be stored in a separate array. The data in the plurality of arrays can collectively be utilized by the computer 522 to generate a B-scan, for example.

Computer 522 can include additional software and/or computer-executable code to process intensity data and generate, for example, image data 140 from FIG. 1. In addition, computer 522 can include computer-executable instructions to carry out the functions of the neuropathy analysis apparatus 130 described above. In this regard, the neuropathy analysis apparatus 130 and the imaging apparatus 120 in FIG. 1 can be implemented by system 500 or other similarly constructed system.

Exemplary Computing Device

Figure 6:
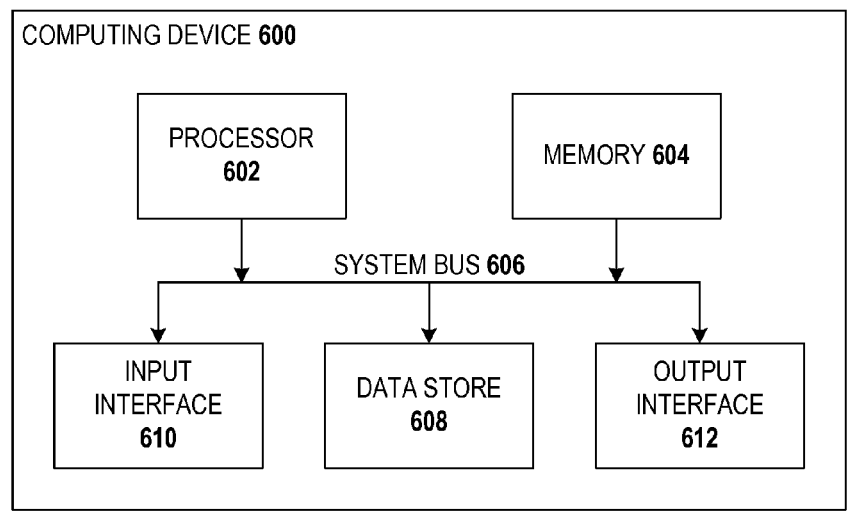
FIG. 6 illustrates a block diagram of an exemplary, non-limiting computing device or operating environment in which one or more aspects of various embodiments described herein can be implemented.

Referring now to FIG. 6, a high-level illustration of an exemplary computing device 600 that can be used in accordance with the systems and methodologies disclosed herein is illustrated. The computing device 600 includes at least one processor 602 that executes instructions that are stored in a memory 604. The instructions may be, for instance, instructions for implementing functionality described as being carried out by one or more components discussed above or instructions for implementing one or more of the methods described above. The processor 602 may access the memory 604 by way of a system bus 606.

The computing device 600 additionally includes a data store 608 that is accessible by the processor 602 by way of the system bus 606. The computing device 600 also includes an input interface 610 that allows external devices to communicate with the computing device 600. For instance, the input interface 6910 may be used to receive instructions from an external computer device, from a user, etc. The computing device 600 also includes an output interface 6712 that interfaces the computing device 600 with one or more external devices. For example, the computing device 600 may display text, images, etc. by way of the output interface 612.

Additionally, while illustrated as a single system, it is to be understood that the computing device 600 may be a distributed system. Thus, for instance, several devices may be in communication by way of a network connection and may collectively perform tasks described as being performed by the computing device 600.

Moreover, the acts described herein may be computer-executable instructions that can be implemented by one or more processors and/or stored on a computer-readable storage medium or media. The computer-executable instructions can include a routine, a sub-routine, programs, a thread of execution, and/or the like. Still further, results of acts of the methodologies can be stored in a computer-readable storage medium, displayed on a display device, and/or the like.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the term "exemplary" is intended to mean "serving as an illustration or example of something."

Various functions described herein can be implemented in hardware, software, or any combination thereof. If implemented in software, the functions can be stored on or transmitted over as one or more instructions or code on a computer-readable medium. Computer-readable media includes both computer-readable storage media and communication media including any medium that facilitates transfer of a computer program from one place to another. A computer-readable storage media can be any available media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Also, a connection can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Illustrative embodiments have been described, hereinabove. It will be apparent to those skilled in the art that the above devices and methods may incorporate changes and modifications without departing from the general scope of the claimed subject matter. It is intended to include all such modifications and alterations within the scope of the claimed subject matter. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method for detecting and monitoring an optic neuropathy of a retina, comprising:
    obtaining imaging data of a region of the retina;
    identifying boundaries between layers of the retina in the region based on the imaging data; and
    determining, on a location-by-location basis for at least a portion of the region of the retina, a measurement value related to ratio value (R) between a total backscattered signal intensity of one or more target layers of the retina and a total backscattered signal intensity of one or more reference layers to generate a set of measurement values for locations in the portion of the region of the retina, wherein the measurement value is generally monotonic with respect to an integrated attenuation value ($\mu_{ATT}d$) such that R is used as a proxy measurement for $\mu_{ATT}d$, which is determined according to the following relation:

$$\mu_{ATT}d = \frac{\log(R/\beta + 1)}{2},$$

where
$\beta$ is modeled as a substantially constant value,
R is the ratio value, and
$\mu_{ATT}d$ represents a total attenuation of light over a depth d of the retina.

2. The method of claim 1, wherein the set of measurement values are a set of integrated attenuation values calculated location-by-location.

3. The method of claim 2, further comprising:
    standardizing a depth over which the total backscattered signal intensity of the one or more reference layers is determined from location to location,
    wherein the standardizing facilitates maintaining $\beta$ as a substantially constant value.

4. The method of claim 3, wherein the ratio value R for a particular location, with standardization of the depth over which the total backscattered signal intensity of the one or more reference layers, is given by:

$$R = \frac{T_{IRL}}{T_{ref}}$$

$$\approx \frac{\sum_{z=1}^{d_{IRL}} T_{IRL}(z)}{\frac{1}{d_{ref}} \sum_{z=1}^{d_{ref}} T_{ref}(z)},$$

where
$T_{IRL}(z)$ is a signal intensity of a backscattered signal from the one or more target layers at depth z, $T_{ref}(z)$ is a signal intensity of a backscattered signal from the one or more reference layers at depth z,
$d_{IRL}$ is a thickness of the one or more target layers, and
$d_{ref}$ is a thickness of the one or more reference layers.

5. The method of claim 1, wherein the one or more target layers include a retinal nerve fiber layer, a ganglion cell layer, an inner plexiform layer, or combinations thereof.

6. The method of claim 1, wherein the one or more reference layers include a retinal pigment epithelium.

7. The method of claim 1, wherein the region of the retina includes at least one of an optic disc or a macula of the retina.

8. The method of claim 1, wherein the imaging data comprises optical coherence tomography (OCT) scan data.

9. The method of claim 1, further comprising displaying information derived from at least one of the set of measurement values or the imaging data.

10. The method of claim 9, wherein displaying the information comprises displaying a visual representation of the set of measurement values as an overlay on image generated from the imaging data.

11. The method of claim 1, further comprising:
    respectively comparing measurement values from the set of measurement values to one or more thresholds; and
    calculating a probability of an optic neuropathy based on comparison results.

12. The method of claim 11, wherein the one or more thresholds are pre-determined from a normative database.

13. The method of claim 1, wherein the imaging data is three-dimensional.

14. The method of claim 1, wherein the imaging data is obtained using a circumpapillary scan.

15. A method for detecting and monitoring an optic neuropathy of a retina, comprising:
    acquiring imaging data for a region of interest of the retina;
    segmenting the imaging data to identify layer boundaries between layers of the retina; and
    calculating, based on segmented imaging data, a set of integrated attenuation values over at least a portion of the region of interest on a location-by-location basis, integrated attenuation values ($\mu_{ATT}d$), of the set of integrated attenuation values, being based on ratio values, for respective locations, between a total backscattered signal intensity of one or more target layers of the retina and a total backscattered signal intensity of one or more reference layers,
    wherein each of the integrated attenuation values is determined according to the following relation:

$$\mu_{ATT}d = \frac{\log(R/\beta + 1)}{2},$$

where
$\beta$ is modeled as a substantially constant value,
R is the ratio value, and
$\mu_{ATT}d$ represents a total attenuation of light over a depth d of the retina.

16. The method of claim 15, wherein the imaging data is optical coherence tomography (OCT) scan data.

17. The method of claim 15, further comprising:
    comparing the set of integrated attenuation values to normative data; and
    outputting a probability of an optic neuropathy based on a result of comparing the set of integrated attenuation values to normative data.

18. The method of claim 17, further comprising constructing the normative data by:
collecting a plurality of optical coherence tomography (OCT) scans on a plurality of confirmed normal subjects,
aggregating measurements from the plurality of OCT scans, and
statistically compiling aggregated measurements.

19. The method of claim 15, wherein the imaging data is three-dimensional.

20. The method of claim 15, wherein the imaging data is acquired using a circumpapillary scan.

21. A method for detecting and monitoring an optic neuropathy of a retina, comprising:
obtaining imaging data of a region of the retina;
identifying boundaries between layers of the retina in the region based on the imaging data;
determining, on a location-by-location basis for at least a portion of the region of the retina, a measurement value related to ratio value (R) between a total backscattered signal intensity of one or more target layers of the retina and a total backscattered signal intensity of one or more reference layers to generate a set of measurement values for locations in the portion of the region of the retina;
respectively comparing integrated attenuation values from the set of integrated attenuation values to one or more thresholds; and
calculating a probability of an optic neuropathy based on comparison results.

22. The method of claim 21, wherein the one or more thresholds are pre-determined from a normative database.

23. The method of claim 21, further comprising:
standardizing a depth over which the total backscattered signal intensity of the one or more reference layers is determined from location to location,
wherein the standardizing facilitates maintaining β as a substantially constant value.

24. The method of claim 23, wherein the ratio value R for a particular location, with standardization of the depth over which the total backscattered signal intensity of the one or more reference layers, is given by:

$$R = \frac{T_{IRL}}{T_{ref}}$$

$$\approx \frac{\sum_{z=1}^{d_{IRL}} T_{IRL}(z)}{\frac{1}{d_{ref}} \sum_{z=1}^{d_{ref}} T_{ref}(z)},$$

where
$T_{IRL}(z)$ is a signal intensity of a backscattered signal from the one or more target layers at depth z,
$T_{ref}(z)$ is a signal intensity of a backscattered signal from the one or more reference layers at depth z,
$d_{IRL}$ is a thickness of the one or more target layers, and
$d_{ref}$ is a thickness of the one or more reference layers.

25. The method of claim 21, wherein the one or more target layers include a retinal nerve fiber layer, a ganglion cell layer, an inner plexiform layer, or combinations thereof.

26. The method of claim 21, wherein the one or more reference layers include a retinal pigment epithelium.

27. The method of claim 21, wherein the region of the retina includes at least one of an optic disc or a macula of the retina.

28. The method of claim 21, wherein the imaging data comprises optical coherence tomography (OCT) scan data.

29. The method of claim 21, further comprising displaying information derived from at least one of the set of measurement values or the imaging data.

30. The method of claim 21, wherein the integrated attenuation value is generally monotonic with respect to the ratio value.

31. The method of claim 21, wherein the imaging data is three-dimensional.

32. The method of claim 21, wherein the imaging data is obtained using a circumpapillary scan.

* * * * *